United States Patent
Colston, Jr. et al.

(10) Patent No.: US 7,993,266 B2
(45) Date of Patent: Aug. 9, 2011

(54) EARLY DETECTION OF CONTAGIOUS DISEASES

(75) Inventors: Billy W. Colston, Jr., San Ramon, CA (US); Fred P. Milanovich, Lafayette, CA (US); Pedro Estacio, Mission San Jose, CA (US); John Chang, Walnut Creek, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 1233 days.

(21) Appl. No.: 10/375,273

(22) Filed: Feb. 26, 2003

(65) Prior Publication Data
US 2003/0204130 A1    Oct. 30, 2003

Related U.S. Application Data

(60) Provisional application No. 60/375,986, filed on Apr. 26, 2002.

(51) Int. Cl.
*A61B 5/00* (2006.01)
(52) U.S. Cl. ............. 600/300; 340/573.1; 128/903; 128/920
(58) Field of Classification Search ......... 600/300–301; 128/903–904, 920
See application file for complete search history.

(56) References Cited

U.S. PATENT DOCUMENTS

| | | | |
|---|---|---|---|
| 6,473,038 B2 | 10/2002 | Patwari et al. | |
| 6,569,092 B1 * | 5/2003 | Guichon et al. | 600/300 |
| 6,610,012 B2 * | 8/2003 | Mault | 600/300 |
| 7,427,920 B2 * | 9/2008 | Martin et al. | 340/573.1 |
| 2002/0107008 A1 | 8/2002 | Hendrey et al. | |
| 2002/0125999 A1 * | 9/2002 | Cho et al. | 340/286.02 |
| 2003/0009088 A1 | 1/2003 | Korth et al. | |

OTHER PUBLICATIONS

Author Unknown, "Ekahau—The Most Accurate Location in Wireless Networks," web page http://www.ekahau.com/, Ekahau, Inc., (2000-2003), 1 page.
Ferscha, A., et al., "Location Awareness in Community Wireless LANs," Workshop, GI/OCG—Jahrestagung 2001, Vienna, Austria, (Sep. 2001), 6 pages.
Pradhan, S., et al., "Websign: hyperlinks from a physical location to the web," Hewlett-Packard Laboratories Palo Alto, Jun. 11, 2001 (internal accession date only), (2001).

* cited by examiner

*Primary Examiner* — Michael C Astorino
(74) *Attorney, Agent, or Firm* — John P. Wooldridge

(57) ABSTRACT

This invention provides an electronic proximity apparatus and a surveillance method using such an apparatus for alerting individuals that are exposed to a contagious disease. When a person becomes symptomatic and is diagnosed as positive for a given contagious agent, individuals that have recently maintained a threshold proximity with respect to an infected individual are notified and advised to seek immediate medial care. Treatment of individuals in the very early phases of infection (pre-symptomatic) significantly reduces contagiousness of the infected population first exposed to the contagious disease, thus preventing spread of the disease throughout the general population.

19 Claims, 4 Drawing Sheets

EARLY DETECTION OF CONTAGIOUS DISEASES

RELATED APPLICATION

This application claims the benefit of U.S. Provisional Application No. 60/375,986, filed Apr. 26, 2002, and entitled, "Method for Early Detection of Contagious Diseases," which is incorporated herein by this reference.

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to a system and method for detecting and responding to an outbreak of contagious diseases. More specifically, the present invention provides a proximity method and system for monitoring individuals through identification devices embedded in pagers, cell phones, or similar devices from which infected individuals can be notified and advised to seek immediate medical care.

2. State of Technology

Current surveillance systems and methods to prevent the outbreak of contagious diseases rely on post-symptomatic reporting, and therefore are severely limited in what portion of the population they can treat or isolate before infection becomes widespread and uncontrollable. In general, individuals are most infectious when they first begin to develop symptoms. Vaccinations work if the vaccine is available to the individual before infection and the prevalence of the disease warrants the risks associated with the vaccine's side effects. Therefore, a surveillance solution to prevent diseases transmitted by person-to-person interaction before the specific disease becomes epidemic is greatly desired.

Background information on an existing technology that relies on positional context information between people and inanimate objects, i.e., to detect a user's presence in the proximity of a specific physical entity, is contained in "*Websigns: Hyperlinking Physical Locations to the Web*", by Pradhan et al., *IEEE Computer*, Vol. 34, Number 8 (August 2001), pp. 42-46, including the following: "[b]y using a simple form of augmented reality, the system allows users to visualize service related to physical objects of interest." Additional information on context aware systems is contained in "*Location Awareness in Community Wireless LANs*", by Fersha et al., Workshop, GI/ÖCG-Jahrestagung 2001, Vienna, Austria, September 2001, including the following: "we have extended the collection and exploitation of awareness information from the users physical activities in the campus workspace, like movement within and among offices or lecture halls, walking among buildings on campus, etc. Using a combination of IEEE 802.11 WLAN and RFID tagging technologies for enhanced position tracking of mobile devices thus allows for a seamless integration of user activities aside the interaction with desktop computing facilities into a shared virtual workspace opening a whole new dimension of awareness abilities."

Various existing tracking systems are capable of monitoring the presence of people or assets. Background information on such a system can be found in, "*Ekahau—The Most Accurate Location in Wireless Networks*". Ekahau, Inc. 2000-2002 Available: http://www.ekahau.com, including the following: "Ekahau Positioning Engine (EPE) is a powerful Java-based positioning server that provides PC and PDA location coordinates (x, y, floor) and tracking features to client applications."

Background information on a system and method that utilizes peer-to-peer proximity measurements together with a known geographical position can be found in, U.S. Pat. No. 6,473,038 B2, titled "Method and Apparatus for Location Estimation," issued Oct. 28, 2002 to Patwari et al., including the following: "a system and method operate to provide location estimates for mobile devices. The system does not require a great deal of installed infrastructure. Moreover in the case of urban canyons and inside buildings where there are numerous obstructions to the propagation of signals (e.g., GPS signals), the system is able to function to provide location information for devices that might otherwise be out of range."

Accordingly, the present invention provides a solution for preventing outbreaks of contagious diseases by a method and apparatus for monitoring person-to-person interactions.

SUMMARY OF THE INVENTION

Accordingly, the present invention provides a method that is capable of distributing to a plurality of individuals in a region a personal apparatus that is capable of measuring signals emitted from similar devices. By downloading and analyzing proximity information received from the personal apparatus of a person diagnosed with a contagious disease, one can determine if notifying such individuals of exposure to the diagnosed disease is needed.

Another aspect of the present invention is to provide a pre-symptomatic surveillance and alert detector that enables proximity information from personal apparatus to be analyzed for contagious disease identification, tracking, and/or notification.

Another aspect of the present invention provides a pre-symptomatic surveillance and alert network that includes a plurality of personal apparatus that is widely dispersed within a region, at least one mobile proximity data and analysis storage unit that is capable of collectively analyzing downloaded proximity data received from each of the plurality of apparatus, and a system administrator that can also collectively analyze downloaded proximity data received from each of the plurality of personal apparatus and that is equally capable of analyzing downloaded proximity data from the mobile proximity data and analysis storage units for contagious disease identification, tracking, and/or notification.

Accordingly, the invention provides a pre-symptomatic surveillance and alert method and apparatus to prevent diseases transmitted by person-to-person interaction before a specific disease becomes epidemic. Such an invention provides medical personnel and scientists the capability of studying and preventing the spread of infectious diseases living in close proximity such as nursing homes and military bases and on a large scale by integration into devices, such as, for example, cell phones, that will additionally allow wide regional pre-symptomatic surveillance to prevent the spread of deadly diseases.

BRIEF DESCRIPTION OF THE DRAWINGS

The accompanying drawings, which are incorporated into and form a part of the disclosure, illustrate an embodiment of the invention and, together with the description, serve to explain the principles of the invention.

DETAILED DESCRIPTION OF THE INVENTION

Referring now to the following detailed information, and to incorporated materials; a detailed description of the invention, including specific embodiments, is presented. The detailed description serves to explain the principles of the invention.

Unless otherwise indicated, all numbers expressing quantities of ingredients, constituents, reaction conditions and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical value, however, inherently contain certain errors necessarily resulting from the standard deviation found in their respective testing measurements.

General Description

The present invention provides a pre-symptomatic surveillance method and apparatus for detecting and responding to an outbreak of contagious diseases that are transmitted primarily through person-to-person contact, such as, but not limited to, viral infections like influenza, or bacterial infections like staphylococcus, or biological agents such as Ebola. This response is possible by monitoring proximity and time durational interaction of individuals through electronic identification devices that may, as one example, be embedded in portable commercially available apparatus such as, but not limited to, pagers, cell phones, personal digital assistants, or similar personal devices.

By following the present invention's protocol method of identification and notification of exposed individuals upon a positive diagnosis of an individual that carries such a device taught in the present invention, and by treatment of identified individuals who respond to notification in the early phases of infection (i.e., pre-symptomatic), the present invention reduces contagiousness of an infected populace and prevents the spread of the disease throughout the general population.

Specific Description

Figure 1:
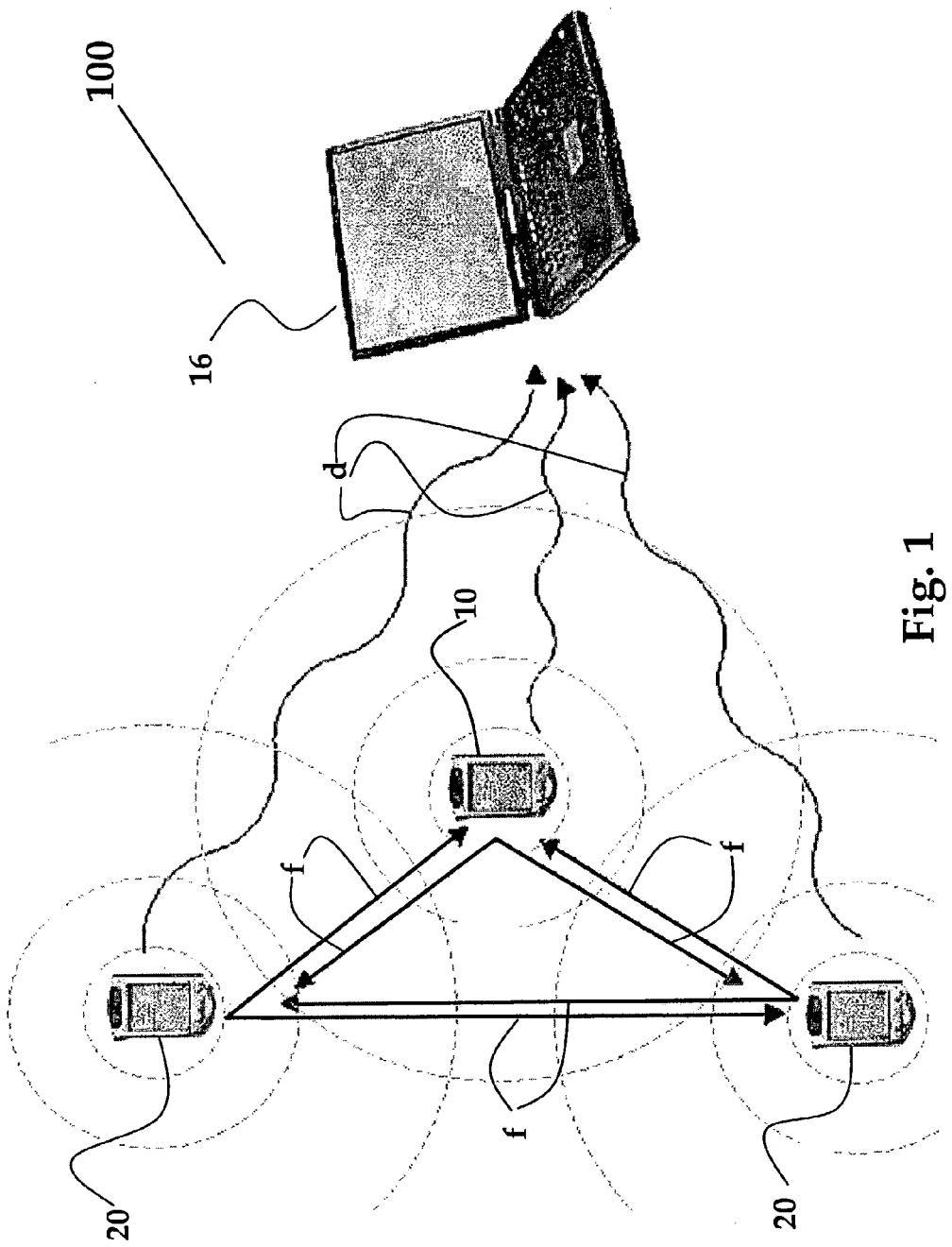
FIG. 1 shows an example of a pre-symptomatic surveillance detector of the present invention.

FIG. 1 shows an example of a pre-symptomatic surveillance detector of the present invention and is generally designated by the reference numeral 100. Detector 100 includes a peer-to-peer personal apparatus 10 and a central storage unit 16 (e.g., a laptop computer), which is capable of having proximity and time durational data downloaded (denoted by d) from one or more additional peer-to-peer personal apparatus 20 for collective analysis with apparatus 10 that have transmitted and or received data (denoted by f) by a large area wireless network (LAN), as detailed hereinafter. Personal apparatus 10 may be constructed from commercially available electronic components that can include a transmitter (not shown), a receiver (not shown), and a data storage device (not shown) that collectively serves as a monitor and a storage device for transmitted proximity and time durational interaction information. In an example method of using such a detector 100, personal apparatus 10 measures and stores the strength of, for example, radio frequency signals emitted by other personal apparatus 20 and communicates that information to a central storage unit 16, which is capable of displaying a user notification if the device is targeted for disease exposure. Central storage unit 16 retrieves proximity and time durational interaction information from each personal apparatus 10, 20 and stores it in a database. The raw data can subsequently be retrieved from the database and used for epidemiological study and modeling.

In an additional arrangement, detector 100 as shown in FIG. 1, may include commercial wireless interfaces, such as but not limited to, infrared or microwave technologies that also allow integration into available portable personal devices, such as, but not limited to, cell phones, pagers, personal identification cards, laptops, and Personal Digital Assistants (e.g., a handheld personal computer made by Compaq (i.e., an iPAQ)).

For example, a wireless network, such as Bluetooth, a registered trademark of Bluetooth SIG, INC., Corporation by Assignment, Delaware, located in Washington D.C., may be used in the peer-to-peer communication system of the present invention. The wireless network can include an open standard for short-range transmission of digital voice and data between mobile devices (laptops, PDAs, phones), and desktop devices that supports point-to-point and multipoint applications. Such a technology is built into a small microchip and operates in a globally available frequency band (i.e., 2.4 GHz), ensuring communication compatibility worldwide. Bluetooth, incorporating a radio transceiver, such as a microchip, is capable of being integrated into the personal devices of the present invention to facilitate fast and secure transmission of both voice (e.g., if equipped or modified into a cell phone) and data, even when the devices are not within line of sight.

As another example, a wireless technology, such as, but not limited to, International Electronic and Electrical Engineers (IEEE) 802.11a or IEEE 802.11b, may additionally be incorporated into the present invention as the communication standard based on its present common use in both business and home environments that enables users high-speed access to networks and the Internet while roaming throughout an area. Such a wireless technology, employing, for example, IEEE 802.11b, can also operate at a frequency of 2.4 GHz with a maximum data rate of 11 Mbps. Moreover, several new protocols for wireless LAN such as IEEE 802.15, IEEE 802.16, and others, are also ready for introduction for use in wireless LAN systems and may be considered as a protocol for the communication standard of the present invention.

In one embodiment, each personal apparatus 10 (e.g., an iPAQ) as shown in FIG. 1, is equipped with an IEEE 802.11b Wireless LAN PC Card for exchanging device identification information with other personal apparatus 20 (e.g., iPAQs), in the system and for downloading stored proximity and time durational data to central storage unit 16. Each iPAQ personal apparatus 10, 20, periodically sends out a radio frequency (RF) ping broadcast. To determine its proximity to other users, apparatus 10 iPAQ measures the signal strength of other personal apparatus 20 iPAQs' RF broadcasts. In free space, the intensity of an RF signal diminishes with increased distance, at a rate roughly proportional to the inverse of the square of the distance. Thus, by applying a precise relationship between signal strength and proximity for the devices, one can gauge proximity using signal strength measurements. A proximity algorithm is applied in post processing. Personal apparatus 10 iPAQ sends a packet of information central storage unit 16 containing the signal strength, the time of measurement, the detected device's identification information, and the host's identification information. Central storage unit 16 can utilize a structured query non-commercial, commercial, or modified commercial language software, such as but not limited to MySQL, to store all proximity data transmitted by the iPAQs into a data base and is based upon the concept of categorizing personal interactions into at least three operator controlled proximity bands discussed hereinafter.

Figure 2:
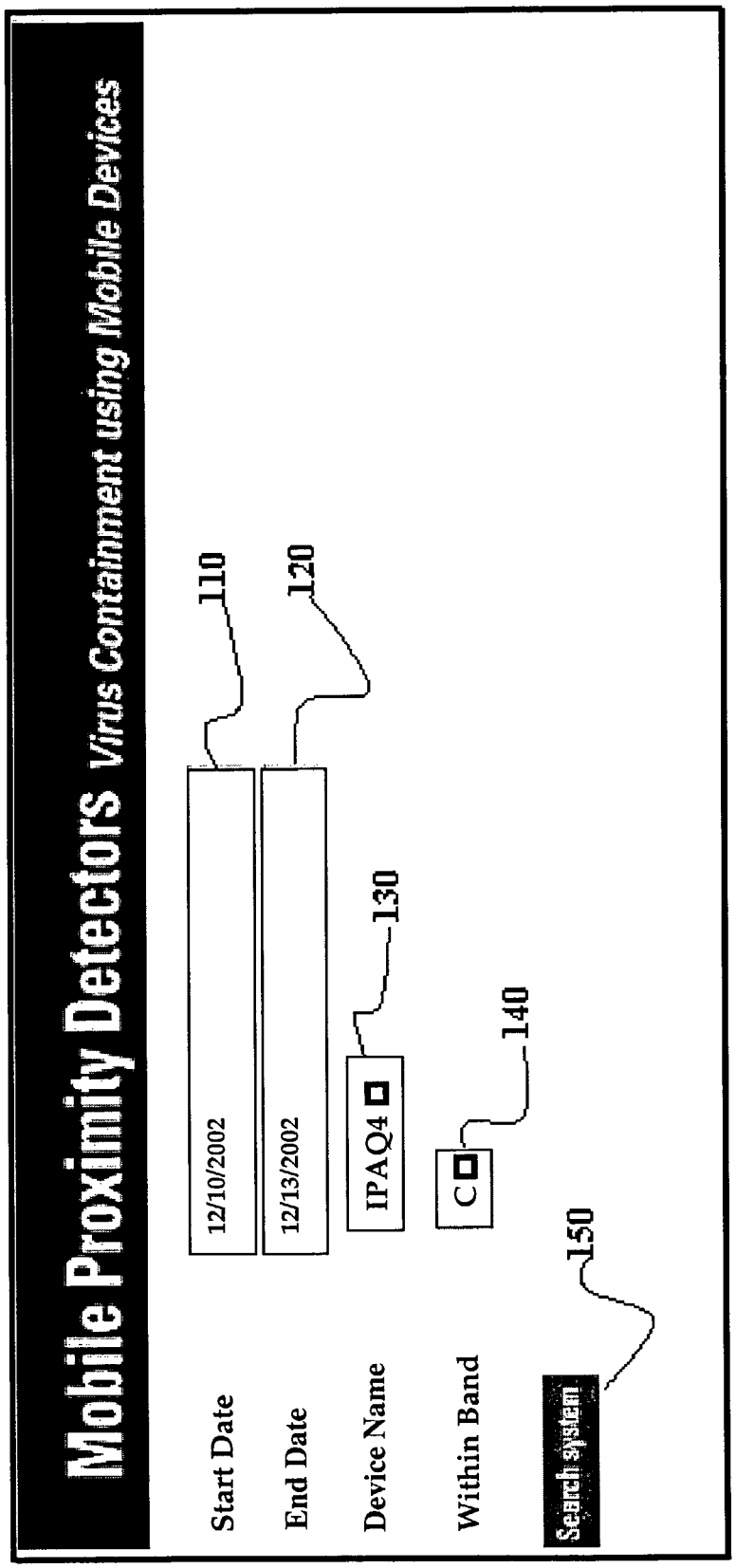
FIG. 2 shows a software screenshot of an example program medical personnel may use in analyzing proximity data.

FIG. 2 shows an example of a software screenshot wherein an individual carrying a personal apparatus, such as an iPAQ, with ID# 4, is diagnosed with a disease on Dec. 13, 2002. Based on knowledge of the disease characteristics and the progression of the disease in the diagnosed individual, medical personnel determine that the individual probably became contagious on Dec. 10, 2002. A professional, such as, for example, a medical doctor or scientist, then queries the network to determine what other individuals may be at risk. On the form as shown in FIG. 2, start and end dates 110, 120 are specified for the time period that the individual may have transmitted the disease to others. The device name 130 corresponds to the device identification number of the iPAQ carried by the diagnosed individual. Finally, a proximity band 140 is specified. The distance range of interest for the study of disease transmission between individuals is about up to 15 feet. The reduced to practice embodiment has a range of up to 150 feet, but by utilizing technologies such as Bluetooth, ranges of up to 333 feet are capable of being monitored by such devices of the present invention depending on signal fluctuation, multi-path effects, reflections off objects, device variation, and body position relative to detected devices. The ranges shown in the following selected bands are only given as examples and may vary depending on the specific disease or diseases that necessitates surveillance and containment. Referring back to FIG. 2, if Band A is specified, the results will report time durational interaction of only those who have been in close proximity, e.g., up to about 6 feet, to the infected individual. If Band B is selected, the results will report time durational interaction of only those who have been in medium proximity, e.g., between about 5 to about 20 feet, to the infected individual. If Band C is selected, time durational interaction of all devices detected by the iPAQ #4 in a long band range, e.g., greater than 15 feet to the infected individual, will be displayed in the results.

Figure 3:
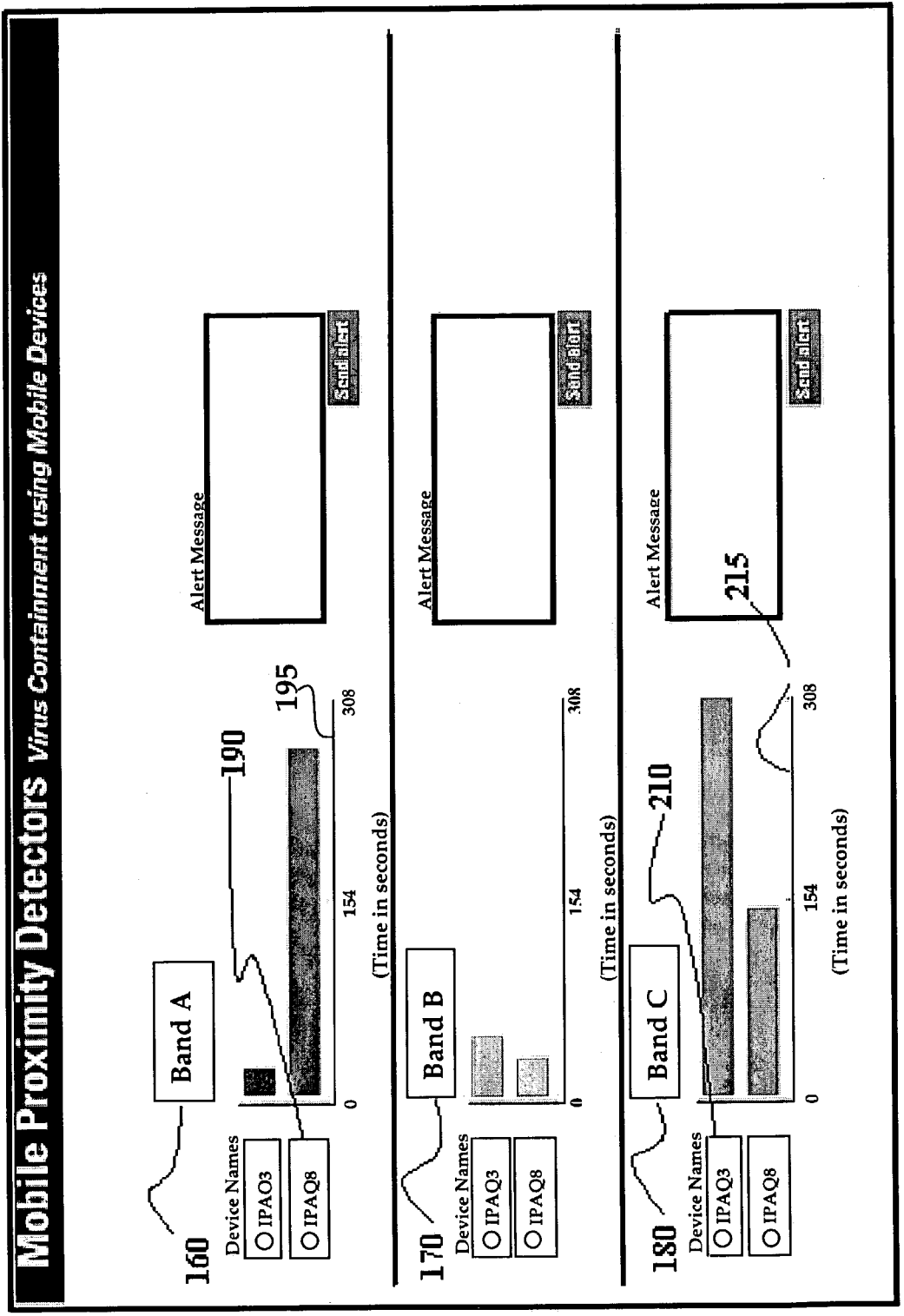
FIG. 3 illustrates a software screenshot of resulting proximity history of interacting devices.

FIG. 3 illustrates a software screenshot example of the proximity history of devices that iPAQ #4 interacted with when a user presses the "Search System" button 150, as shown in FIG. 2. Devices detected within each of the three proximity bands (e.g., close proximity Band A 160, medium proximity Band B 170, and long-Range Proximity Band C 180) during the specified contagious period, as shown in FIG. 2 (i.e., 110, 120), are shown in FIG. 3 with their corresponding time bar durational interaction (e.g., time bars 195, 215) to represent the amount of time spent within each proximity band. FIG. 3 shows that the user of iPAQ #8 190 became exposed in close proximity (i.e., Band A 160) to the infectious individual for several minutes as denoted by the time bar 195. FIG. 3 additionally shows that the user of iPAQ #3 210 also interacted with the infected individual for a long time period, as denoted by time bar 215, however the majority of interaction time is within long-range proximity band 180. From this data, the medical professional might decide to alert the user of iPAQ #8 190 of their risk of exposure to the disease. Medical professionals using the example software do not require knowledge of any personal details of either the infected individual or those who were exposed to the disease. Likewise, individuals who are alerted of their exposure are not informed of the identity of the diagnosed individual.

Figure 4:
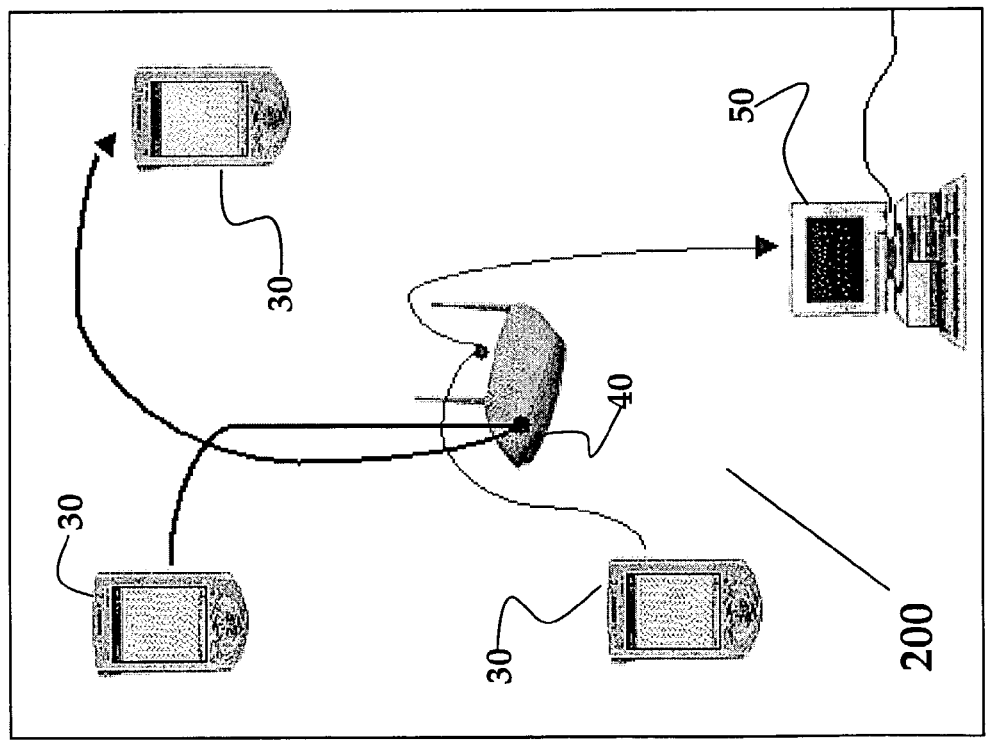
FIG. 4 shows a pre-symptomatic surveillance and alert network embodiment.

Turning to FIG. 4, a pre-symptomatic surveillance and alert network embodiment that utilizes an infrastructure mode, and is generally designated by the reference numeral 200, includes personal apparatus 10 as shown in FIG. 1 and the various wireless telecommunications protocol possibilities (e.g., Bluetooth and IEEE 802.11b), but incorporates a larger number of such personal apparatus 30 (i.e., nodes) that can number, as one embodiment, greater than about 2, more often greater than about 10, and even more often, greater than about 1000, in which all personal apparatus 30 communicate through a single node (e.g., a laptop computer 16 with wireless communication capabilities as shown in FIG. 1) called the access point 40. Access point 40 is necessary in order to bridge wireless devices such as personal apparatus 30 to a wired network 50 and the Internet.

As another example embodiment, a pre-symptomatic surveillance and alert network embodiment may be arranged as a Mesh or ad-hoc structure, where a bridge 40 and a wired network 50, as shown in FIG. 4, is not required. Such a network, which includes a plurality of personal apparatus, such as personal digital assistants, laptops, or similar personal devices coupled with a central storage unit that can number, as one embodiment, greater than about 2, more often greater than about 10, and even more often, greater than about 1000, has desired qualities over an infra-structure network, as shown in FIG. 4 because they do not require a fixed infrastructure and are easier and less expensive to deploy.

Figure 5:
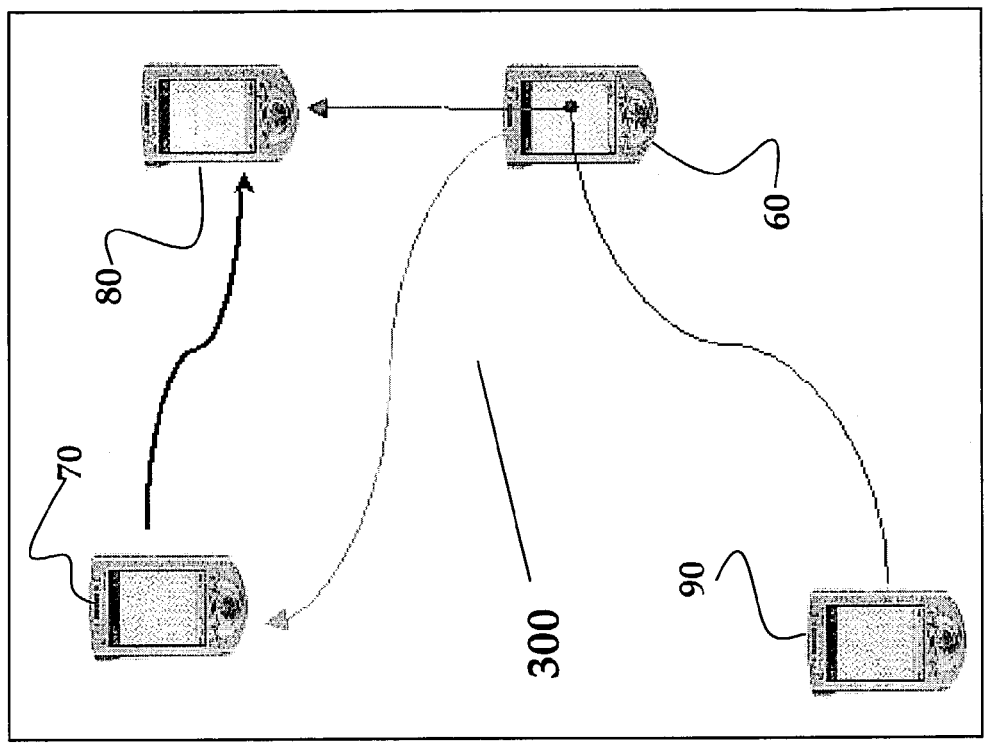
FIG. 5 illustrates a multi-hop ad-hoc network.

FIG. 5 illustrates a multi-hop ad-hoc network 300, in which a node (e.g., a personal apparatus 60) may relay messages through other nodes (e.g., personal apparatus 70, 80), in order to communicate with, for example, a personal apparatus 90 (i.e., a node) that is out of range. Although such a multi-hop functionality may also be added to extend the range (e.g., greater that 150 feet) over which a personal apparatus may download its data, their functionality is more limited in that without a bridge to a wired network, nodes in this arrangement do not have access to the Internet. Additionally, routing algorithms become complex for large networks. In the event of failure of the central data and analysis storage unit, such as a laptop, the nodes (i.e., personal apparatus) continue to collect proximity and time durational interaction data. The system's functionality may be compromised, however, because instead of downloading the data to a central location, each personal apparatus (e.g., iPAQ) instead saves the data in a local file. A system administrator, such as, but not limited to, a PDA, a laptop, a personal computer, or any system capable of downloading the data from a plurality of personal apparatus, 60, 70, 80, 90 and additionally capable of analysis, tracking and/or notification by communication via the internet, is therefore unable to view all the collected data until the laptop functionality is restored or the data is retrieved directly from the personal apparatus.

In a pre-symptomatic surveillance and alert method constructed to principles of the present invention, a personal apparatus that includes a transmitter, a receiver, and a data storage device, serves as a proximity monitor to transmit, receive, and store information, such as, but not limited to, identification, distance, location, and time interaction duration of the proximity measurements. Next, some portion of the early victims who contract a contagious disease will become symptomatic and apply for medical care. Screening such patients by diagnosing the disease or diseases contracted involves a variety of medical procedures. Presently, diagnosis for many diseases is guesswork based on oral patient history and physical symptoms. Discrimination between viral and bacterial agents is particularly challenging, since both agents often elicit the same gross physiological response. However, novel technologies exist that allow multiplex (i.e., one sample, many measurements) measurements. One such technology, for example, is the Affymetrix DNA chip, which allows up to thousands of disease biomarkers from a single drop of blood. Expense, complexity and a host of other factors have prevented such a technology from finding immediate application in clinics and hospitals but it is one such technology that is capable of being incorporated into the diagnosis step of the present invention.

Regardless of the diagnosis method, by diagnosing individuals for such a contagious disease and by downloading a database from a data collection and analysis storage unit, such as for example, a laptop computer, of an infected individual's personal apparatus (i.e., proximity monitor), medical personnel may opt for notifying high risk individuals via a remote retrieval device, such as by a cell phone, a wireless modem, or a pager, after inputting such data into a disease specific algorithm (e.g., MySQL). Such a software program can account for factors such as, input relative proximity, duration, and location values of other identified devices as part of its algorithm. Treating such individuals by administering drugs such as antiviral agents, vaccines, and/or antibiotics to curtail the spread of the host infection and the spread of the disease to others is especially beneficial early in the incubation process of the disease. If the nature of the disease is only suspect or the therapeutics may have significant adverse side effects, further laboratory tests may be necessary before an individual is treated.

Accordingly, regardless of the response, the method of the present invention provides a practical means for pre-symptomatic surveillance and detection of contagious diseases of small to large populations of individuals.

It should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A pre-symptomatic surveillance and alert method, comprising:
    distributing a separate personal apparatus to each human of a plurality of humans in a region, wherein each said apparatus comprises a proximity transceiver and a data storage device, wherein said proximity transceiver comprises means for transmitting proximity data to a computer controller and to each other said separate personal apparatus during a data acquisition time period, wherein said proximity transceiver further comprises means for receiving a notification from said controller;
    diagnosing a contagious disease in at least one infected human of said plurality of humans;
    downloading to said computer controller said proximity data from each said apparatus to produce downloaded data, wherein said computer controller analyzes said downloaded data to determine if at least one human of said plurality of humans requires notification, wherein notification is required if the personal apparatus of said at least one human is located within a predefined distance from the personal apparatus of said at least one infected human, wherein said computer controller further comprises means for transmitting said notification to the personal apparatus of said at least one human;
    analyzing with said computer controller said downloaded data to determine if said at least one human of said plurality of humans requires said notification; and
    transmitting said notification to the personal apparatus of said at least one human if said notification is required.

2. The method of claim 1, further comprising treating said at least one human for said contagious disease.

3. The method of claim 1, wherein said proximity transceiver and said storage device are integrated into a personal apparatus selected from the group consisting of a cell phone, a pager, a personal identification card, a laptop computer, and a personal digital assistants (PDA).

4. The method of claim 1, wherein said proximity transceiver uses radio frequencies.

5. The method of claim 1, wherein said proximity transceiver uses optical frequencies.

6. The method of claim 1, wherein said proximity transceiver uses a wireless communication standard.

7. The method of claim 6, wherein said wireless communication standard includes IEEE802.

8. The method of claim 6, wherein said wireless communication standard includes a frequency band of about 2.4 GHz.

9. The method of claim 1, wherein said proximity transceiver has an operating range of up to 150 feet.

10. The method of claim 1, wherein said proximity transceiver has an operating range of up to 333 feet.

11. A pre-symptomatic surveillance and alert system, comprising:
    a computer controller; and
    a plurality of personal apparatuses, wherein each personal apparatus of said plurality of personal apparatuses comprises a proximity transceiver and a data storage device, wherein said proximity transceiver comprises means for transmitting proximity data to said computer controller and to other said personal apparatuses during a data acquisition time period, to produce downloaded data, wherein said proximity transceiver further comprises means for receiving a notification from said computer controller, wherein said computer controller analyzes said downloaded data to determine if at least one human of said plurality of humans requires notification, wherein notification is required if a diagnosis is made of a contagious disease in at least one infected human of said plurality of humans and the personal apparatus of said at least one human is located within a predefined distance from the personal apparatus of said at least one infected human, wherein said computer controller further comprises means for transmitting said notification to the personal apparatus of said at least one human.

12. The network of claim 11, wherein said proximity transceiver and said storage device are integrated into a personal device selected from the group consisting of a cell phone, a pager, a personal identification card, a laptop and a personal digital assistant.

13. The network of claim 12, wherein said transceiver utilizes radio frequencies.

14. The network of claim 12, wherein said transceiver utilizes optical frequencies.

15. The network of claim 12, wherein said transceiver is adapted to operate using a wireless communication standard.

16. The network of claim 15, wherein said wireless communication standard includes IEEE802 technology.

17. The network of claim 15, wherein said wireless communication standard includes a frequency band of about 2.4 GHz.

18. The network of claim 11, wherein each said personal apparatus comprises a multi-hop functionality to extend a communication range.

19. The network of claim 11, where said computer controller is integrated into a laptop computer.

* * * * *